(12) United States Patent
Li et al.

(10) Patent No.: US 12,714,375 B2
(45) Date of Patent: Aug. 25, 2026

(54) EXAMINATION TABLE AND X-RAY IMAGING SYSTEM

(71) Applicant: GE Precision Healthcare LLC, Waukesha, WI (US)

(72) Inventors: Fusheng Li, Beijing (CN); Yuqing Li, Beijing (CN); Youbao Cao, Beijing (CN); Lingzhi Zhou, Beijing (CN); Gang Hong, Beijing (CN)

(73) Assignee: GE Precision Healthcare LLC, Waukesha, WI (US)

( * ) Notice: Subject to any disclaimer, the term of this patent is extended or adjusted under 35 U.S.C. 154(b) by 146 days.

(21) Appl. No.: 18/891,663

(22) Filed: Sep. 20, 2024

(65) Prior Publication Data

US 2025/0099047 A1 Mar. 27, 2025

(30) Foreign Application Priority Data

Sep. 22, 2023 (CN) ......................... 202311243289.5

(51) Int. Cl.
*A61B 6/04* (2006.01)
*A61B 6/00* (2024.01)
*A61B 90/00* (2016.01)

(52) U.S. Cl.
CPC ............ *A61B 6/0407* (2013.01); *A61B 6/547* (2013.01); *A61B 2090/3941* (2016.02)

(58) Field of Classification Search
CPC ..... A61B 6/0407; A61B 6/547; A61B 6/0487; A61B 6/08
See application file for complete search history.

(56) References Cited

U.S. PATENT DOCUMENTS 5,636,259 A * 6/1997 Khutoryansky ..... A61B 6/4283 378/197
2012/0275570 A1* 11/2012 Li .......................... A61B 6/583 378/155
2017/0065246 A1* 3/2017 Lee ...................... A61B 6/4405

* cited by examiner

*Primary Examiner* — Casey Bryant

(57) ABSTRACT

The present application provides an examination table including a table panel assembly, a detector assembly carrying a detector and being capable of moving the detector relative to the table panel assembly, and a detector position indicating apparatus. The detector assembly includes a coverage area constituting an imaging region. The detector position indicating apparatus includes at least one light transmitting plate provided in a non-imaging region of the table panel assembly, and at least one light emitting unit fixed to the detector assembly, the at least one light emitting unit comprising an indicator light, and light emitted by the indicator light being capable of passing through the at least one light transmitting plate to indicate a current position of the detector.

12 Claims, 11 Drawing Sheets

EXAMINATION TABLE AND X-RAY IMAGING SYSTEM

CROSS-REFERENCE TO RELATED APPLICATIONS

This application is based on and claims priority to Chinese Application No. 202311243289.5, filed on Sep. 22, 2023, the entire contents of which is herein incorporated by reference.

TECHNICAL FIELD

The present invention relates to medical imaging technology, and specifically to an examination table and an X-ray imaging system.

BACKGROUND

In an X-ray imaging system, radiation from an X-ray source is emitted toward a subject, and the subject under examination is usually a patient in a medical diagnosis application. Some of the radiation passes through the subject under examination and impacts a detector, which is divided into a matrix of discrete elements (e.g., pixels). The detector elements are read to generate an output signal on the basis of the amount or intensity of radiation that impacts each pixel region. The signal can then be processed to generate a medical image that can be displayed for review, and the medical image can be displayed in a display apparatus of the X-ray imaging system.

For a decubitus scanning mode, typically, the subject under examination needs to lie on an examination table in a decubitus position. The examination table includes a base and a table panel. The table panel is floatingly mounted on the base. The detector is mounted within the space between the table panel and the base, and the table panel can move relative to the base, so as to cause a region of interest of the subject under examination to reach the region of the detector.

SUMMARY

The present invention provides an examination table and an X-ray imaging system.

The exemplary embodiments of the present invention further provide an examination table. The examination table comprises a table panel and a detector cartridge. The detector cartridge is used to carry a detector, and is capable of moving the detector relative to the table panel, a coverage area of the detector constituting an imaging region. The examination table further comprises a detector position indicating apparatus. The detector position indicating apparatus comprises at least one light transmitting plate provided in a non-imaging region of the table panel and at least one light emitting unit fixed to the detector cartridge. The at least one light emitting unit comprises an indicator light, and light emitted by the indicator light is capable of passing through the light transmitting plate to indicate a current position of the detector.

The exemplary embodiments of the present invention further provide an X-ray imaging system. The X-ray imaging system comprises an examination table. The examination table comprises a table panel and a detector cartridge. The detector cartridge is used to carry a detector, and is capable of moving the detector relative to the table panel, a coverage area of the detector constituting an imaging region. The examination table further comprises a detector position indicating apparatus. The detector position indicating apparatus comprises at least one light transmitting plate provided in a non-imaging region of the table panel and at least one light emitting unit fixed to the detector cartridge. The at least one light emitting unit comprises an indicator light, and light emitted by the indicator light is capable of passing through the light transmitting plate to indicate a current position of the detector.

Other features and aspects will become apparent from the following detailed description, drawings, and claims.

BRIEF DESCRIPTION OF THE DRAWINGS

The present invention can be better understood by means of the description of the exemplary embodiments of the present invention in conjunction with the drawings, wherein.

DETAILED DESCRIPTION

Specific embodiments of the present invention will be described below. It should be noted that in the specific description of said embodiments, for the sake of brevity and conciseness, the present description cannot describe all of the features of the actual embodiments in detail. It should be understood that in the actual implementation process of any embodiment, just as in the process of any one engineering project or design project, a variety of specific decisions are often made to achieve specific goals of the developer and to meet system-related or business-related constraints, which may also vary from one embodiment to another. Furthermore, it should also be understood that although efforts made in such development processes may be complex and tedious, for a person of ordinary skill in the art related to the content disclosed in the present invention, some design, manufacture, or production changes made on the basis of the technical content disclosed in the present disclosure are only common technical means, and should not be construed as the content of the present disclosure being insufficient.

Unless defined otherwise, technical terms or scientific terms used in the claims and description should have the usual meanings that are understood by those of ordinary skill in the technical field to which the present invention belongs.

The terms "first" and "second" and similar terms used in the description and claims of the patent application of the present invention do not denote any order, quantity, or importance, but are merely intended to distinguish between different constituents. The terms "one" or "a/an" and similar terms do not express a limitation of quantity, but rather that at least one is present. The terms "include" or "comprise" and similar words indicate that an element or object preceding the terms "include" or "comprise" encompasses elements or objects and equivalent elements thereof listed after the terms "include" or "comprise", and do not exclude other elements or objects. The terms "connect" or "link" and similar words are not limited to physical or mechanical connections, and are not limited to direct or indirect connections.

Figure 1:
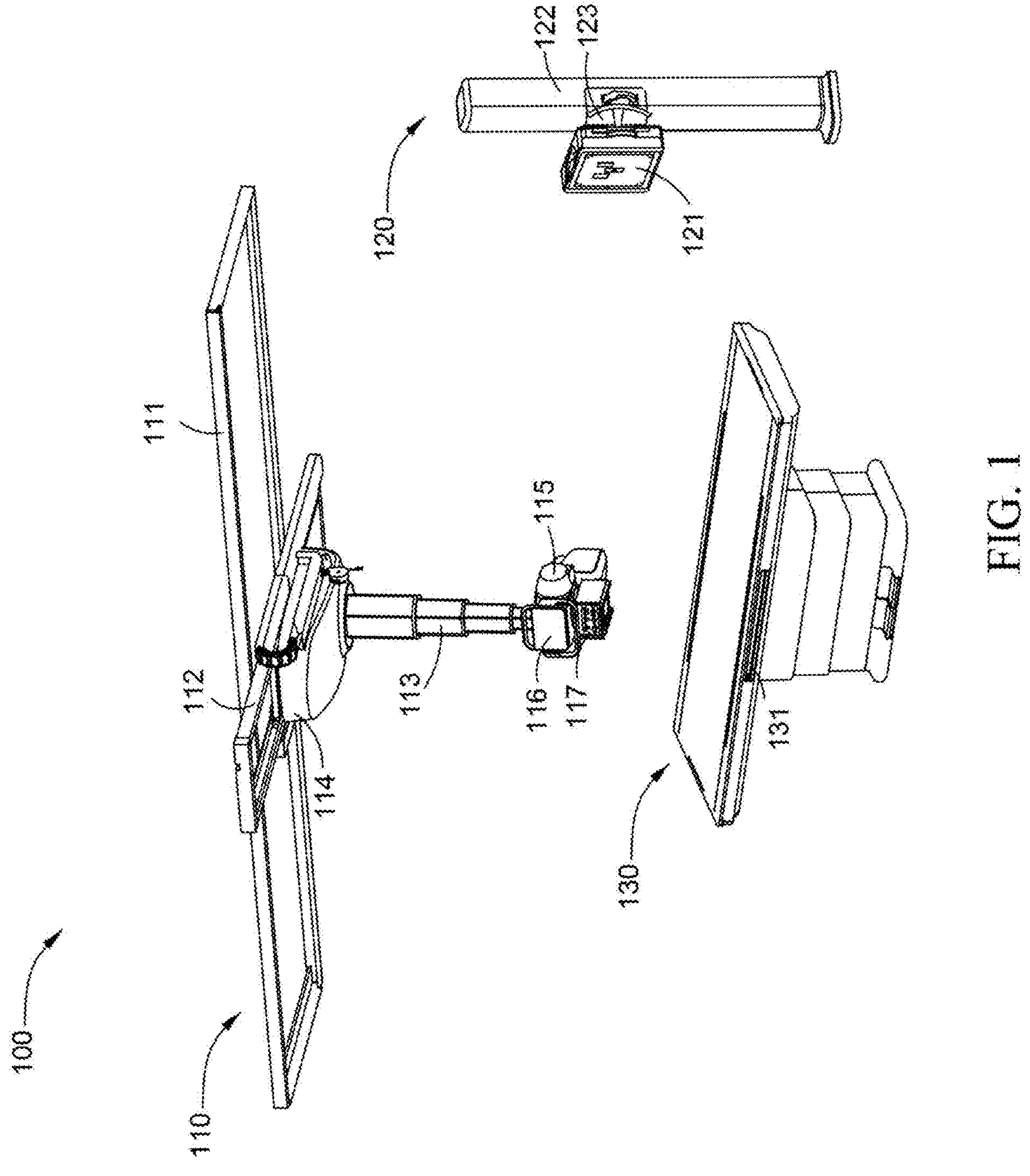
FIG. 1 is a schematic diagram of an X-ray imaging system according to some embodiments of the present invention.

FIG. 1 shows an X-ray imaging system 100 according to some embodiments of the present invention. As shown in FIG. 1, FIG. 1 shows the X-ray imaging system 100 according to some embodiments of the present invention. As shown in FIG. 1, the X-ray imaging system 100 includes a suspension apparatus 110, a wall stand apparatus 120, and an examination table apparatus 130. The suspension apparatus 110 includes a longitudinal guide rail 111, a transverse guide rail 112, a telescopic cylinder 113, a sliding member 114 and a tube assembly 115.

For ease of description, in the present application, the x-axis, y-axis and z-axis are defined such that the x-axis and y-axis are located in the horizontal plane and perpendicular to one another, and z-axis is perpendicular to the horizontal plane. Specifically, the direction in which the longitudinal guide rail 111 is located is defined as the x-axis, the direction in which the transverse guide rail 112 is located is defined as the y-axis direction, and the direction of extension of the telescopic cylinder 113 is defined as the z-axis direction, the z-axis direction being the vertical direction.

The longitudinal guide rail 111 and the transverse guide rail 112 are perpendicularly arranged, the longitudinal guide rail 111 being mounted on a ceiling and the transverse guide rail 112 being mounted on the longitudinal guide rail 111. The telescopic cylinder 113 is configured to carry the tube assembly 115.

The sliding member 114 is provided between the transverse guide rail 112 and the telescopic cylinder 113. The sliding assembly 114 may include components such as a rotating shaft, a motor, and a reel, etc. The motor can drive the reel to rotate around the rotating shaft, which in turn drives the telescopic cylinder 113 to move along the z-axis and/or slide relative to the transverse guide rail. The sliding member 114 is capable of sliding relative to the transverse guide rail 112, i.e., the sliding member 114 is capable of driving the telescopic cylinder 113 and/or the tube assembly 115 to move in the y-axis direction. Further, the transverse guide rail 112 can slide relative to the longitudinal guide rail 111, which in turn drives the telescopic cylinder 113 and/or the tube assembly 115 to move in the x-axis direction.

The telescopic cylinder 113 includes a plurality of cylinders having different inner diameters, and the plurality of cylinders can be sleeved, sequentially from bottom to top, in the cylinder located thereabove, thereby achieving telescoping, and the telescopic cylinder 113 can be telescopic (or movable) in the vertical direction, i.e., the telescopic cylinder 113 can drive the tube assembly to move along the z-axis direction. The lower end of the telescopic cylinder 113 is further provided with a rotating part, and the rotating part can drive the tube assembly 115 to rotate.

The tube assembly 115 includes an X-ray tube, and the X-ray tube may produce X-rays and project the X-rays to an intended region of interest (ROI) of a patient. Specifically, the X-ray tube may be positioned adjacent to a beam limiter, the beam limiter being used to align the X-rays with the intended region of interest of the patient. At least a portion of the X-rays may be attenuated by means of the patient, and may be incident on a detector 121/131.

The suspension apparatus 110 further includes a beam limiter 117, which is usually mounted below the X-ray tube, and X-rays emitted by the X-ray tube irradiate on the body of a subject under examination by means of an opening of the beam limiter 117. An irradiation range of the X-rays, namely the region size of an exposure field of view (FOV), depends on the size of the opening of the beam limiter 117. The locations of the X-ray tube and beam limiter 117 in the transverse direction determine the location of the exposure FOV on the body of the subject under examination. It is well known that X-rays are harmful to the human body, and it is thus necessary to control the X-rays, so that the X-rays only irradiate a site of the subject under examination that needs to be examined, i.e., the region of interest (ROI).

The suspension apparatus 110 further includes a tube console 116, the tube console 116 being mounted on the tube assembly. The tube console 116 includes user interfaces such as a display screen and a control button, used to perform preparation work before image capture, such as patient selection, protocol selection, positioning, etc.

The movement of the suspension apparatus 110 includes the movement of the tube assembly along the x-axis, y-axis, and z-axis, as well as the rotation of the tube assembly in the horizontal plane (the axis of rotation is parallel to or overlaps with the z-axis) and in the vertical plane (the axis of rotation is parallel to the y-axis). In the above motion, a motor is usually used to drive a rotating shaft which in turn drives corresponding components to rotate in order to achieve the corresponding movement or rotation, and the corresponding control components are generally mounted in the sliding member 114. An X-ray imaging unit further includes a motion control unit (not shown in the figure), and the motion control unit can control the described motion of the suspension apparatus 110. Furthermore, the motion control unit can receive a control signal to control a corresponding component to move correspondingly.

The wall stand apparatus 120 includes a first detector assembly 121, a wall stand 122, and a connecting portion 123. The connecting portion 123 includes a support arm that is vertically connected in the height direction of the wall stand 122 and a rotating bracket that is mounted on the support arm, and the first detector assembly 121 is mounted on the rotating bracket. The wall stand apparatus 120 further includes a detector driving apparatus that is arranged between the rotating bracket and the first detector assembly 121, which is driven by the detector driving apparatus to move in a direction parallel to the height direction of the wall stand 122 in the plane held by the rotating bracket, and the first detector assembly 121 can further be rotated relative to the support arm to form an angle with the wall stand. The first detector assembly 121 has a plate-like structure, the orientation of which is variable, facilitating an X-ray incident surface to become vertical or horizontal depending on the incident direction of the X-rays.

A second detector assembly 131 is included on an examination table apparatus 130, and the selection or use of the first detector assembly 121 and the second detector assembly 131 may be determined on the basis of an image capture site of a patient and/or an image capture protocol, or may be determined on the basis of the location of the subject under examination obtained by image capture of a camera, so as to perform image capture and examination in a lying or standing position. FIG. 1 only shows an example diagram of a wall stand and an examination table, and it should be understood by those skilled in the art that wall stands and/or examination tables of any form or arrangement can be selected, or only the wall stand can be mounted, and the wall stand and/or examination table is not intended to limit the overall solution of the present application.

The X-ray imaging system further includes a control apparatus (not shown in the figures), which may be a main control apparatus that is located in a control room, a tube console that is mounted on the suspension apparatus, a mobile or portable control apparatus, or any combination of the above. The control apparatus may include a source control apparatus and a detector control apparatus. The source control apparatus is used to command the X-ray source to emit X-rays for image exposure. The detector control apparatus is used to select a suitable detector among a plurality of detectors, and to coordinate the control of various detector functions, such as automatically selecting a corresponding detector according to the location or pose of the subject under examination. Alternatively, the detector control apparatus may perform various signal processing and filtering functions, specifically, for initial adjustment of a dynamic range, interleaving of digital image data, and the like. In some embodiments, the control apparatus may provide power and timing signals for controlling the operation of the X-ray source and the detector.

In some embodiments, the control apparatus may also be configured to use a digitized signal to reconstruct one or more required images and/or determine useful diagnostic information corresponding to a patient, and the control apparatus may include one or more dedicated processors, graphics processing units, digital signal processors, microcomputers, microcontrollers, application-specific integrated circuits (ASICs), field-programmable gate arrays (FPGAs), or other appropriate processing apparatuses.

Certainly, the X-ray imaging system may further include other numbers or configurations or forms of control apparatuses, for example, the control apparatus may be local (e.g., co-located with one or more X-ray imaging systems 100, e.g., within the same facility and/or the same local network). In other implementations, the control apparatus may be remote, and thus only accessible by means of a remote connection (for example, by means of the Internet or other available remote access technologies). In a specific implementation, the control apparatus may also be configured in a cloud-like means, and may be accessed and/or used in a means that is substantially similar to the means by which other cloud-based systems are accessed and used.

The X-ray imaging system 100 also includes a storage apparatus (not shown in the figures). The control apparatus may store the digitized signal in the storage apparatus. For example, the storage apparatus may include a hard disk drive, a floppy disk drive, a CD-read/write (CD-R/W) drive, a digital versatile disc (DVD) drive, a flash drive, and/or a solid-state storage apparatus. The storage apparatus is used to store a program that can be executed by a computer. Of course, the storage apparatus may also be integrated with the control apparatus, so as to effectively use the footprint and/or meet expected imaging requirements.

In one embodiment, the X-ray imaging system 100 further includes an operator workstation, the operator workstation allowing the user to receive and evaluate the reconstructed image, and input a control instruction (an operation signal or a control signal). The operator workstation may include a user interface (or user input device) in a certain form of operator interface, such as a keyboard, a mouse, a voice activated control apparatus, or any other suitable input device, such that an operator may input an operation signal/control signal to the control apparatus by means of the user interface.

Figure 2:
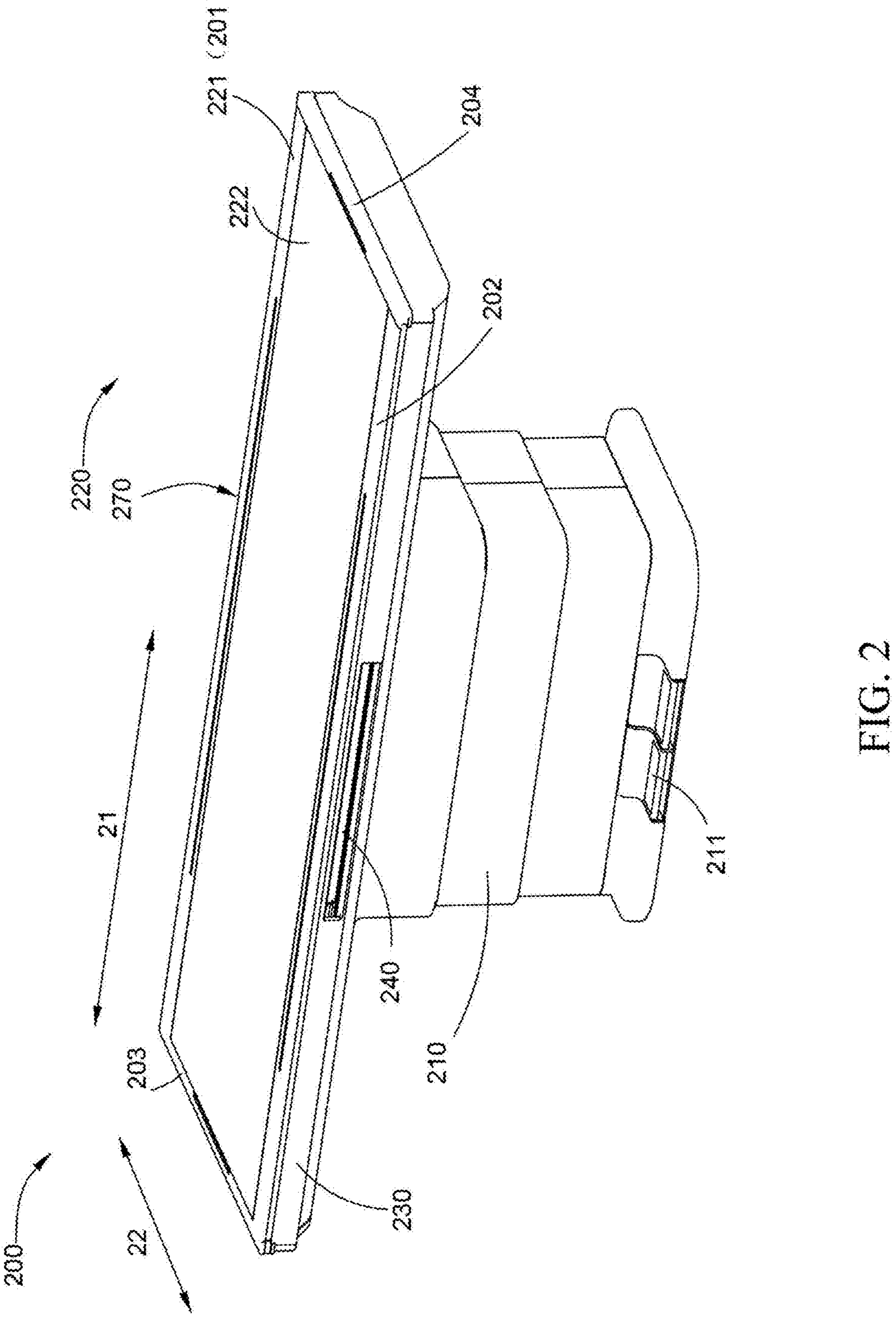
FIG. 2 is a schematic diagram of an examination table according to some embodiments of the present invention.
Figure 3:
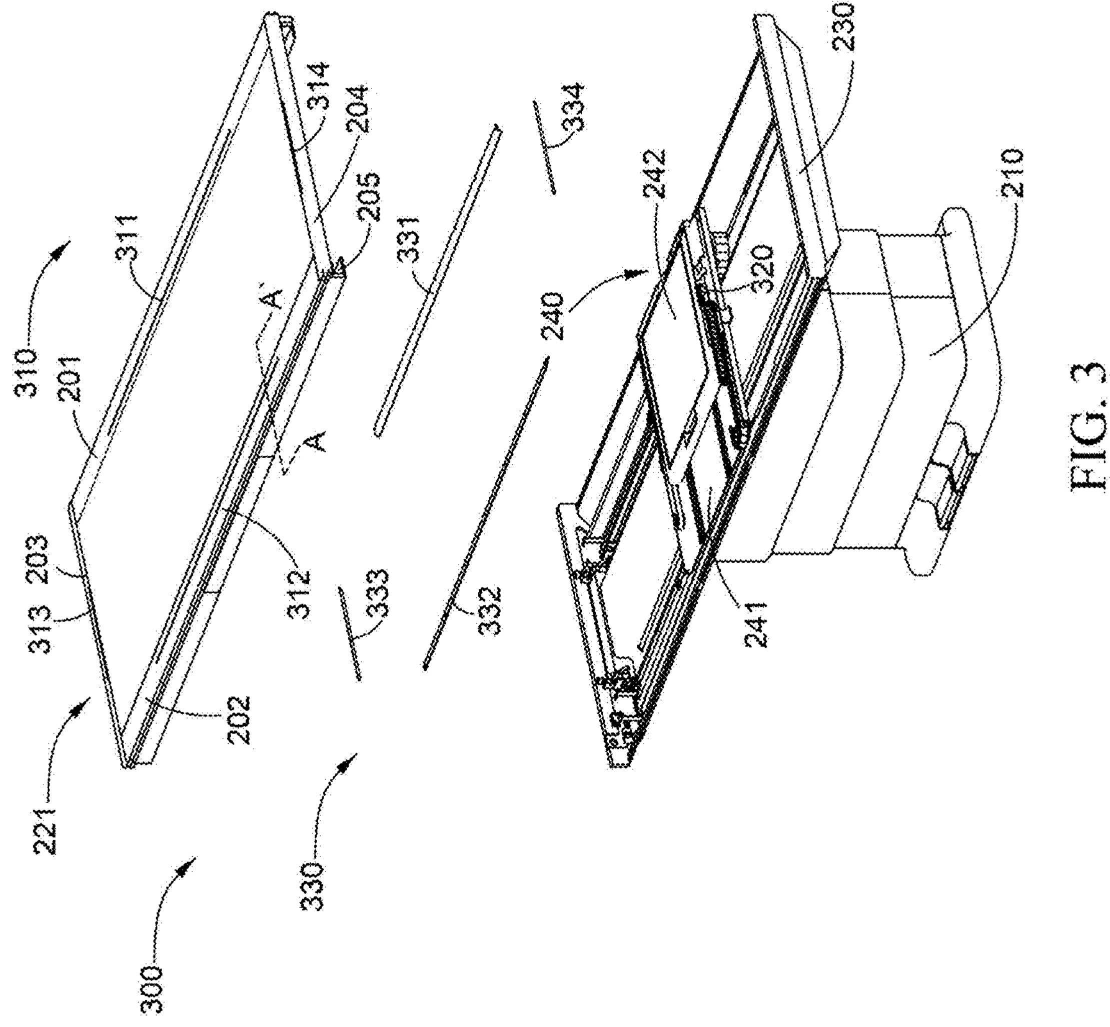
FIG. 3 is an exploded view of an examination table according to some embodiments of the present invention.

FIG. 2 is a schematic diagram of an examination table 200 according to some embodiments of the present invention. FIG. 3 shows an exploded view of an examination table according to some embodiments of the present invention. As shown in FIG. 2 and FIG. 3, the examination table 200 includes a base 210, a table panel assembly 220, a support assembly 230, and a detector assembly 240. For case of description, a direction parallel to a long side of a table panel is referred to as a longitudinal axis 21, and a direction parallel to a short side of the table panel is referred to as a transverse axis 22.

Specifically, the table panel assembly 220 is mounted on the support assembly 230, and an accommodating space is present between the table panel assembly 220 and the support assembly 230, the accommodating space being used to accommodate the detector assembly 240. The detector assembly 240 is mounted on the support assembly 230, and the detector assembly 240 is movable in a transverse direction and/or a longitudinal direction (along the longitudinal axis and/or the transverse axis) relative to the support assembly 230. The support assembly 230 is mounted on the base 210.

In some embodiments, the base 210 has a generally rectangular-shaped, three-dimensional box-like structure, and the base 210 includes a plurality of housings that are sequentially sleeved. The plurality of housings may be sleeved, sequentially from bottom to top, in the housing located thereabove, thereby achieving telescoping so as to adjust the height of the examination table. In some embodiments, the examination table may further include a lifting assembly provided in the base 210. The support assembly 230 can be mounted on a top plate of the lifting assembly. The lifting assembly includes a lifting column and a motor, and power is supplied to the motor to raise or lower the lifting column so as to drive the support assembly to raise or lower the table panel assembly, but the embodiments of the present application are not limited thereto.

Specifically, the base 210 includes a pedal 211, and the pedal 211 can be used to control the height of the examination table, and the user can adjust the height of the examination table by means of controlling the pedal 211. It should be understood by those skilled in the art that the base may also be provided in any other form, for example, the base is provided so that the height cannot be adjusted or the height is adjusted in other forms, and the base is not limited to the above description.

The table panel assembly 220 includes a table panel frame 221 and a table panel 222. The table panel 222 is mounted on the table panel frame 221, and the table panel 222 is movably connected to the table panel frame 221. Specifically, the table panel frame 221 consists of four frames, internally forming a closed space. Specifically, the table panel frame 221 includes a first frame 201, a second frame 202 opposite the first frame 201, and a third frame 203 and a fourth frame 204 adjacent to the first frame 201, the four frames being connected together by means of riveting, welding, key connection, or the like. Certainly, the table panel frame 221 may also be integrally molded. Specifically, the material of the table panel frame 221 is aluminum. Certainly, the table panel frame may also be made of other metal materials. The table panel 222 may be placed on the table panel frame 221, and certainly, may also be inserted in the table panel frame 221 so that an upper surface of the table panel and an upper surface of the table panel frame are in the same plane. Certainly, the table panel 222 may also be rotatably mounted in the table panel frame 221, e.g., the first frame 201 of the table panel frame 221 and a side of the table panel 222 connected to each other forming a rotating shaft 270, so that the table panel 222 can be opened inwards and outwards relative to the rotating shaft 270, and so on.

The table panel 222 may be made using a material having a lower X-ray attenuation, such as being composed of a carbon fiber composite material. The table panel 222 may include a one layer plate or a multilayer plate structure. For example, when the table panel 222 includes the multilayer plate structure, each layer uses a particular material, for example, an inner layer is made of foam and an outer layer is made of a material such as a carbon fiber composite material. Alternatively, a heating layer may be further added to the table panel 222, and heat generated by the heating layer is transferred to the outer layer in contact with the subject under examination. The material has an appropriate strength so as to provide stable support for a scanned object. For details, reference may be made to the prior art, which will not be described again here.

In some non-limiting embodiments, the rotating shaft 270 of the table panel frame 221 and the table panel 222 is arranged along a lengthwise direction of the table panel, i.e., the longitudinal axis 21. That is, the table panel can be flipped outward along the lengthwise direction, that is, one long side of the table panel is fixed, and the other long side can be lifted or lowered. However, it should be understood by those skilled in the art that the rotating shaft may also be arranged in the short side direction of the table panel, that is, the table panel is flipped outward along the width direction.

The detector assembly 240 is mounted on the support assembly 230. The detector assembly 240 includes a tray 241 and a detector cartridge 242. A detector is provided or mounted in the detector cartridge 242. The detector has an X-ray receiving surface capable of receiving X-rays. The detector cartridge 242 is mounted or fixed on the tray 241.

In some embodiments, the detector assembly 240 includes a first group of moving assemblies for driving the detector cartridge 242 to move along the transverse axis 22. Specifically, the detector cartridge 242 can move from a side of the first frame 201 to a side of the second frame 202; therefore, the receiving range of the detector cartridge 242 can be moved along the transverse axis 22 from one side of the table panel to another side.

Specifically, the first group of moving assemblies includes a first group of synchronous belts, a first group of guide rails, and a first motor. The first group of guide rails is arranged along the transverse axis 22, and the bottom of the tray 241 is provided with guide rail slots opposite the first group of guide rails, so that the tray 241 can move relative to the first group of guide rails. One end of the first group of synchronous belts is fixed on the tray 241, and the other end is connected to the first motor, so as to control the first group of synchronous belts to drive the tray to move by means of the first motor, so that the tray and the detector move along the transverse axis 22. Specifically, the first group of moving assemblies further includes at least one first group of sensors to feed back the position of the tray in the transverse axis direction.

Specifically, the detector assembly 240 further includes a second group of moving assemblies, the second group of moving assemblies being used to drive the tray 241 to move the detector cartridge 242 along the longitudinal axis 21. Specifically, the detector assembly 240 can be moved from a side of the third frame 203 to a side of the fourth frame 204; therefore, the receiving range of the detector cartridge 242 can be moved along the longitudinal axis from one side of the table panel to another side.

Specifically, the second group of moving assemblies includes a second group of synchronous belts, a second group of guide rails, and a second motor. The second group of guide rails is arranged along the longitudinal axis 21, and the first group of guide rails is arranged on the second group of guide rails, the first group of guide rails being perpendicular to the second group of guide rails. The tray 241 can move relative to the second group of guide rails. One end of the second group of synchronous belts is fixed on the tray 241, and the other end is connected to the second motor, so as to control the second group of synchronous belts to drive the tray to move by means of the second motor, so as to enable the tray and the detector to move along the longitudinal axis 21. Specifically, the second group of moving assemblies further includes at least one second group of sensors to feed back the position of the tray in the longitudinal direction.

In some embodiments, the coverage area of the detector cartridge constitutes the imaging region. That is, the largest region that the detector can image is the imaging region. Specifically, the area formed by the detector moving along the transverse axis from one side of the table panel to the other side and/or moving along the longitudinal axis from one side to the other side is the imaging region, and the other regions on the table panel assembly are non-imaging regions. In some embodiments, a region where the table panel assembly is located is a non-imaging region.

During use, due to the structural configuration of the examination table, the detector is fixed in the accommodating space between the table panel assembly and the support assembly, and the user or operator cannot accurately learn the real-time position of the detector. When the detector is not aligned with the X-ray source, this may cause a deviation may, thereby affecting image quality. Therefore, the present application provides an indicating apparatus capable of indicating the position of the detector in real time. The apparatus can indicate the position of the detector on the table panel in real time.

In some embodiments, as shown in FIG. 3, a detector position indicating apparatus 300 according to some embodiments of the present application includes at least one light transmitting plate 310 and at least one light emitting unit 320. The at least one light transmitting plate 310 is provided in a non-imaging region of the table panel assembly. The at least one light emitting unit 320 is fixed to the detector assembly. The at least one light emitting unit 320 includes an indicator light, and light emitted by the indicator light is capable of passing through the light transmitting plate 310 to indicate a current position of the detector.

Specifically, the at least one light transmitting plate 310 is provided on any one of the frames of the table panel frame 221 of the table panel assembly 220, and the at least one light emitting unit 320 may be provided on the detector cartridge or on the tray of the detector assembly.

The positions and the number of the light transmitting plates 310 correspond to the positions and the number of the light emitting units 320. Specifically, the number of the light transmitting plates and the number of the light emitting units may be any number. Specifically, there may be only one light transmitting plate and only one light emitting unit provided. For example, one light transmitting plate may be provided on any frame of the table panel frame 221. For example, one light transmitting plate may be provided on the first frame or the second frame along the lengthwise direction of the table panel, and one light emitting unit may be mounted or fixed at the position of the detector cartridge corresponding to the light transmitting plate to indicate the real-time position of the detector. Certainly, two light transmitting plates and two light emitting units may be provided. For example, light transmitting plates may be provided on two adjacent frames of the table panel frame, respectively, and one light emitting unit may be provided at each detector cartridge position corresponding thereto. In addition, light transmitting plates may be provided on two opposite frames of the table panel frame, respectively, and one light emitting unit may be provided at each detector cartridge position corresponding thereto. Certainly, the light transmitting plates and the light emitting units may be provided on any three table panel frames and at detector cartridge positions. Certainly, the light transmitting plate and the light emitting unit may be provided on each table panel frame and at the periphery of each detector cartridge. In the following, a detailed description will be provided via an example wherein four light transmitting plates and four light emitting units are mounted.

Figure 4:
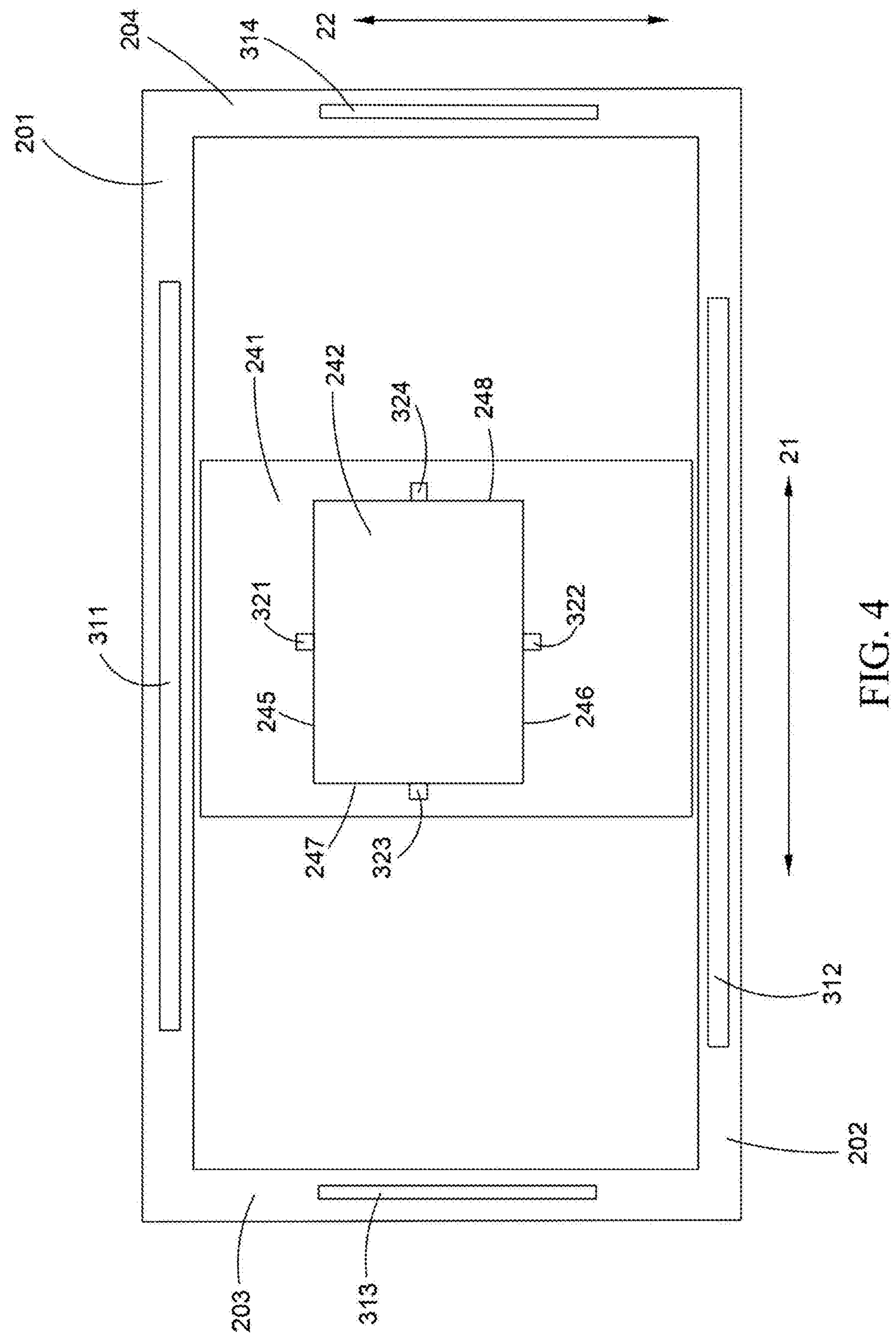
FIG. 4 is a schematic diagram of a detector position indicating apparatus according to some embodiments of the present invention.

FIG. 4 shows a schematic diagram of a detector position indicating apparatus according to some embodiments of the present application. As shown in FIG. 4, four sides of the table panel frame are each provided with one light transmitting plate, and one light emitting unit is correspondingly mounted on four sides of the detector cartridge.

Specifically, in the table panel frame 221, the first frame 201 is provided with a first light transmitting plate 311, the second frame 202 is provided with a second light transmitting plate 312, the third frame 203 is provided with a third light transmitting plate 313, and the fourth frame 204 is provided with a fourth light transmitting plate 314. The detector cartridge 242 includes a first side 245 positioned adjacent to the first frame 201, a second side 246 positioned adjacent to the second frame 202, a third side 247 positioned adjacent to the third frame 203, and a fourth side 248 positioned adjacent to the fourth frame 204. A first light emitting unit 321 is mounted on the first side 245 of the detector cartridge, a second light emitting unit 322 is mounted on the second side 246 of the detector cartridge, a third light emitting unit 323 is mounted on the third side 247 of the detector cartridge, and a fourth light emitting unit 324 is mounted on the fourth side 248 of the detector cartridge.

Specifically, light emitted by the indicator light of the first light emitting unit 321 can be shown or seen via the first light transmitting plate 311, light emitted by the indicator light of the second light emitting unit 322 can be shown or seen via the second light transmitting plate 312, light emitted by the indicator light of the third light emitting unit 323 can be shown or seen via the third light transmitting plate 313, and light emitted by the indicator light of the fourth light emitting unit 324 can be shown or seen via the fourth light transmitting plate 314. A line connecting the position of the light shown by the first light transmitting plate 311 and the position shown by the second light transmitting plate 312 should be parallel to the transverse axis 22, and a line connecting the position of the light shown by the third light transmitting plate 313 and the position shown by the fourth light transmitting plate 314 should be parallel to the longitudinal axis 21. Therefore, the real-time position of the detector can be shown by means of cooperation between the light emitting units and the light transmitting plates that are provided.

In some embodiments, the at least one light emitting unit is mounted at a center position of at least one side of the detector cartridge. Certainly, the at least one light emitting unit may also be mounted at at least one corner of the detector cartridge, and a specific position at which the light emitting unit is mounted is not limited as long as the user knows which specific position of the detector is represented by the indicator light transmitted through the light transmitting plate. Certainly, it is also possible to mount light emitting units at two corners of each side of the detector cartridge, respectively, to show the size or boundary of the entire detector via the light transmitting plate.

Figure 5:
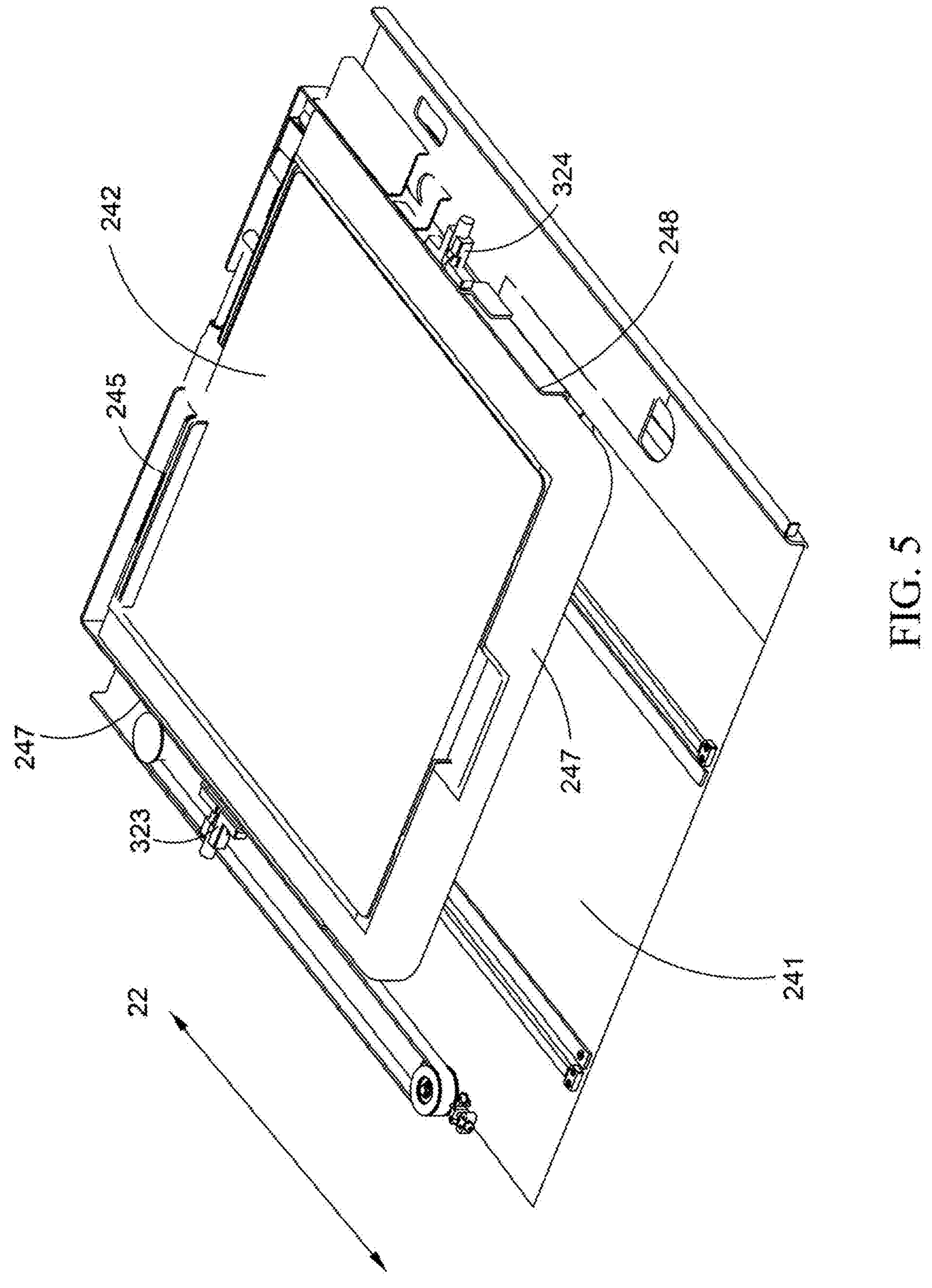
FIG. 5 is a schematic diagram of a front side of a detector assembly in the examination table shown in FIG. 3.
Figure 6:
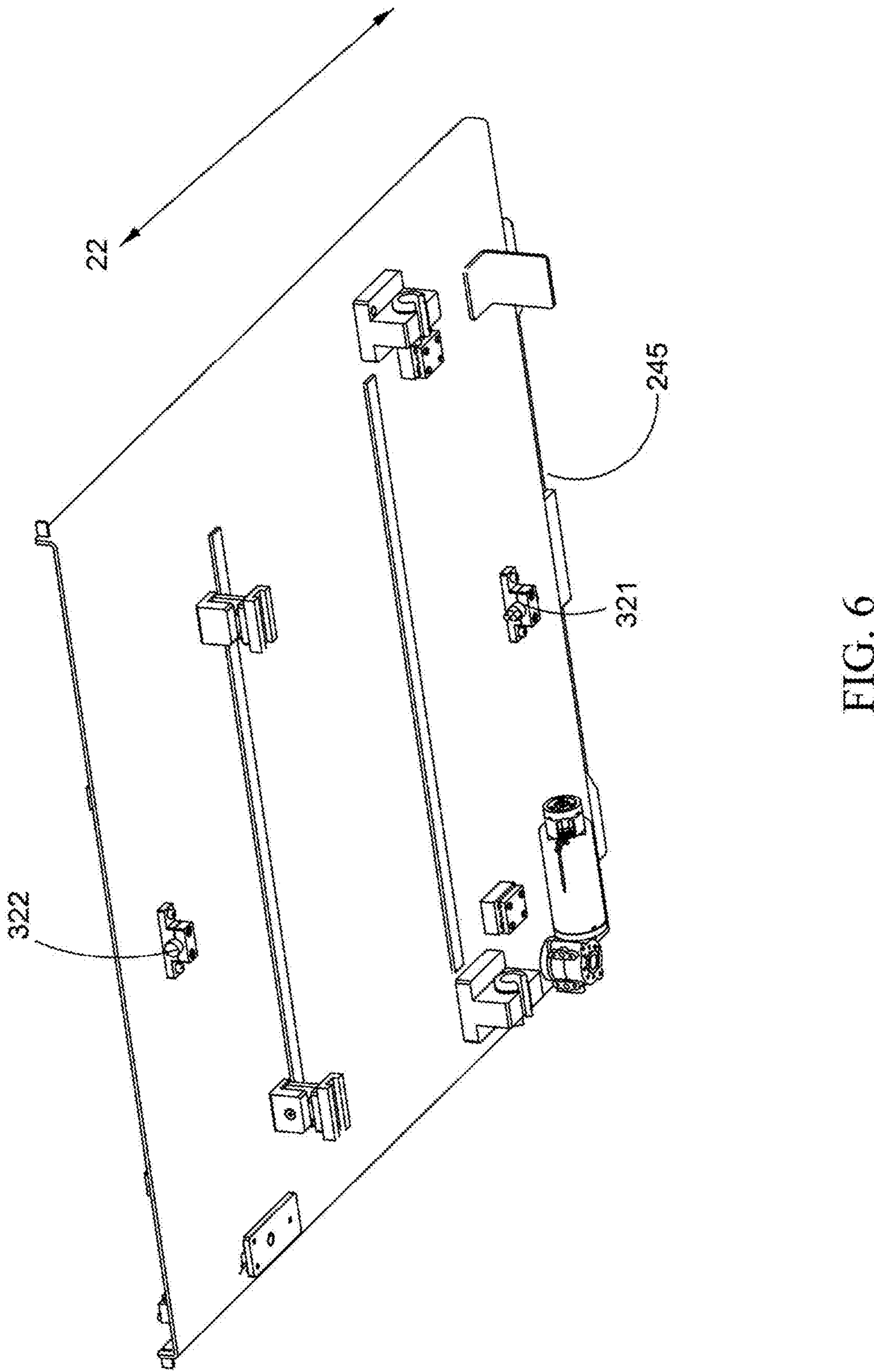
FIG. 6 is a schematic diagram of a rear side of a detector assembly in the examination table shown in FIG. 3.

FIG. 5 shows a schematic diagram of a front side (a top view) of the detector assembly in the examination table shown in FIG. 3, and FIG. 6 shows a schematic diagram of a rear side (a bottom view) of the detector assembly in the examination table shown in FIG. 3.

In some embodiments, as shown in FIG. 5, the two light emitting units provided along the longitudinal axis 21 are mounted at two ends of the detector cartridge, respectively. That is, the third light emitting unit 323 is mounted on the third side 247 of the detector cartridge, and the fourth light emitting unit 324 is mounted on the fourth side 248 of the detector cartridge. As shown in FIG. 6, the two light emitting units provided along the transverse axis 22 are each mounted at the bottom of the tray 241. That is, the first light emitting unit 321 is mounted in a position on the bottom of the tray close to the first side 245 of the detector cartridge, and the second light emitting unit 322 is mounted in a position on the bottom of the tray close to the second side 246 of the detector cartridge. The first light emitting unit and the second light emitting unit are mounted at the bottom of the tray, that is, the two light emitting units provided along the transverse axis are mounted at the bottom, so that during movement of the detector cartridge along the transverse axis 22 relative to the tray, the positions of the light emitting units are prevented from interfering with a moving path, to prevent the light emitting units from colliding with the table panel frame, or to prevent a moving distance of the detector from being affected, or the like.

In addition, the two light emitting units are mounted on the detector cartridge, and the other two light emitting units are mounted at the bottom of the tray, so that during movement of the detector cartridge, the light emitting units can accurately show the position thereof. Specifically, when the detector cartridge needs to move along the longitudinal axis 21, the tray 241 can move relative to the table panel assembly or the support assembly to move the detector. In this case, the positions of the third light emitting unit 323 and the fourth light emitting unit 324 relative to the third light transmitting plate and the fourth light transmitting plate do not change, but the positions of the first light emitting unit 321 and the second light emitting unit 322 mounted at the bottom of the tray change relative to the light transmitting plates, and the light shown by the first light transmitting plate 311 and the second light transmitting plate 312 changes as the detector cartridge moves. Similarly, when the detector cartridge needs to move along the transverse axis 22, the tray 241 does not move, and the detector cartridge 242 can move along the transverse axis relative to the tray 241. In this case, the positions of the first light emitting unit 321 and the second light emitting unit 322 mounted at the bottom of the tray do not change, but the positions of the third light emitting unit 323 and the fourth light emitting unit 324 relative to the third light transmitting plate and the fourth light transmitting plate change, and the light shown by the third light transmitting plate and the fourth light transmitting plate changes as the detector cartridge moves. Certainly, it is also possible for the detector cartridge to move along both the transverse axis and the longitudinal axis, and the light shown by each light transmitting plate can also change as the detector cartridge moves, so as to show the real-time position of the detector.

In some embodiments, the light emitting unit includes a mounting base and the indicator light. The mounting base can be fixed to a side edge of the detector cartridge or the bottom of the tray, and can fix the indicator light in a corresponding position. The indicator light can be fixed in a direction of leaving the detector cartridge. That is, the direction of the light emitted by the indicator light is a direction towards the light transmitting plate.

In some embodiments, the indicator light includes a laser light, and light emitted by the laser light is a laser line having a preset length. The laser line is emitted along a vertical direction. Specifically, in order to further ensure that the laser light can be reflected to be shown via the light transmitting plate, the light emitted by the laser light in the present application is a line, and the line is vertical, so that the light emitted by the indicator light can still be captured and further reflected in the case that a reflecting plate distorted or has an error. The structure of the reflecting plate will be described in further detail later.

Referring back to FIG. 4, in some embodiments, the at least one light transmitting plate is configured to be in an elongated shape, a length of the light transmitting plate being determined by a coverage area of the light emitting unit. Specifically, the light transmitting plate may be an acrylic plate, coated tempered glass, or the like, and the material of the light transmitting plate is not limited as long as the light transmitting plate can transmit light and has a certain shading effect so as to prevent the light from being so bright as to irritate the eyes of users or patients.

In some embodiments, other types of indicator lights, for example, an LED light, may be used as the indicator light, and a light condenser may be additionally provided. The indicator light is not limited to the described types as long as the indicator light can emit a light beam.

In some embodiments, the length of the light transmitting plate is determined according to the movable or coverable area of the light emitting unit or the detector. For example, when a light emitting unit is mounted at a middle position of each side of the detector cartridge, assuming that the detector is currently moved to an upper left corner, i.e., the corner position of the connection between the first frame and the third frame, the position that the first light emitting unit 321 is aligned with may be marked or defined as one end of the first light transmitting plate, and the position that the third light emitting unit 323 is aligned with may be marked or defined as one end of the third light transmitting plate. When the detector is moved to a lower right corner, i.e., the corner position of the connection between the second frame and the third frame, the position that the third light emitting unit 323 is aligned with may be marked or defined as the other end of the third light transmitting plate, and the position that the second light emitting unit 322 is aligned with may be marked or defined as one end of the second light transmitting plate. Similarly, when the detector is moved to the other two extreme positions, the positions of the first light transmitting plate and the fourth light transmitting plate can be determined. Certainly, the length of the light transmitting plate may be set to be slightly greater than the length corresponding to the extreme position of the light emitting unit.

Similarly, when the light emitting unit is not mounted at a middle position of the detector cartridge, the length of the light transmitting plate can also be determined when the detector is in an extreme position.

Figure 7:
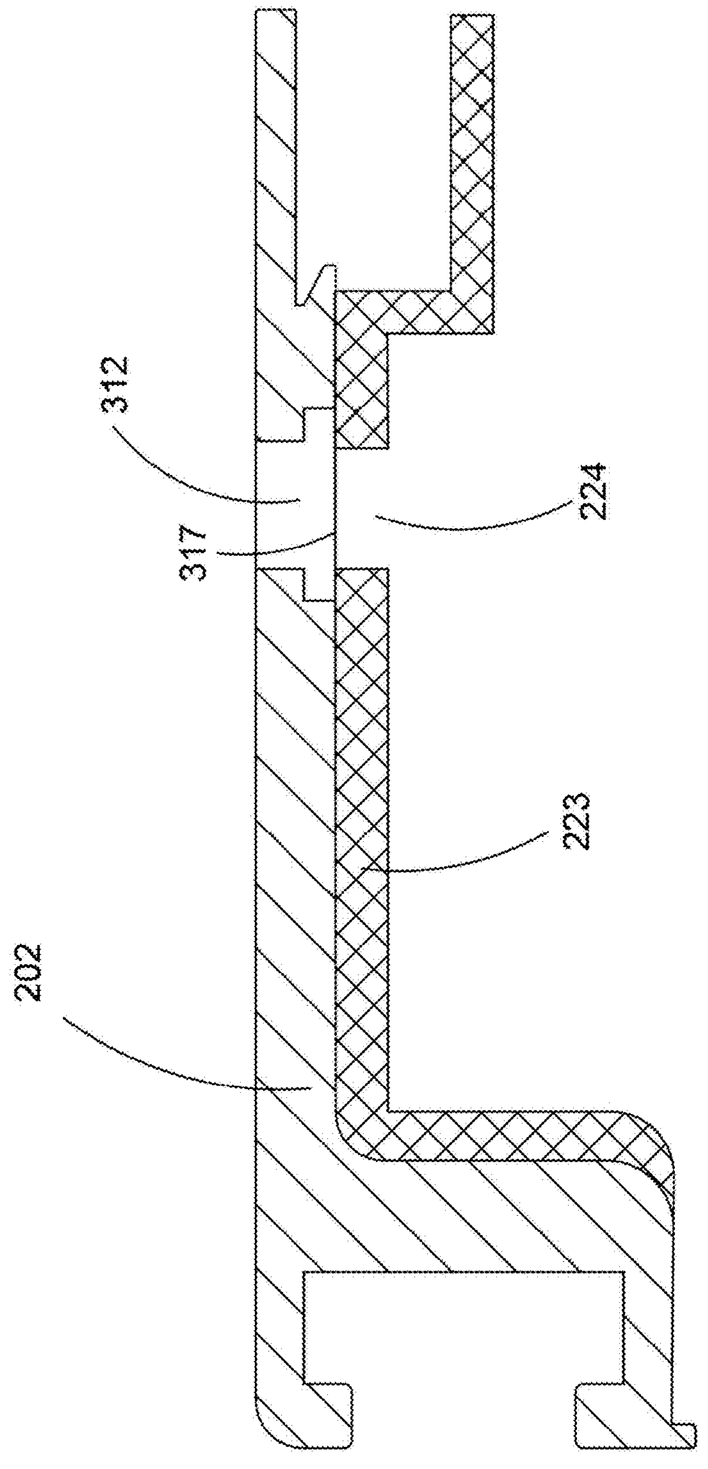
FIG. 7 is a cross-sectional view of a table panel assembly shown in FIG. 3 along A-A'.

In some embodiments, the light transmitting plate is inserted in the table panel frame, i.e., a surface of the top of the light transmitting plate and a surface of the top of the table panel frame are in the same plane (there is no height difference). FIG. 7 shows a cross-sectional view along A-A' in the examination table shown in FIG. 3. As shown in FIG. 7, the second frame 202 and the second light transmitting plate 312 are used as an example. The light transmitting plate 312 has a protruding cross section, and the table panel frame is provided with a recess corresponding to the protruding cross section. The light transmitting plate can be mounted and fixed in the recess.

Similarly, the light transmitting plates all have the cross section shown in FIG. 7. By means of providing a light transmitting plate having the protruding cross section, the light transmitting plate can be fixed in the table panel frame, and is prevented from coming off or falling from the upper surface of the table panel frame.

In some embodiments, the table panel assembly further includes a support plate 223. Specifically, the support plate 223 has substantially the same shape as the table panel frame, and the dimensions of the support plate 223 are substantially the same as or slightly smaller than those of the table panel frame. The support plate 223 is mainly used to carry the table panel and provide reinforcement. The support plate 223 is a metal frame, and is mounted at a lower surface of the table panel frame. In some embodiments, the support plate 223 is provided with at least one slot 224 in order to realize a light path, and the number and positions of the at least one slot 224 correspond to the number and positions of the light transmitting plates. The length of the slot 224 is substantially the same as the length of the light transmitting plate, but the width of the slot 224 is slightly smaller than the width of the light transmitting plate. The support plate is mounted such that not only the table panel is supported, but the light transmitting plate is also fixed, and the light path is realized.

In some embodiments, a side of the light transmitting plate close to the indicator light is further provided with a fluorescent layer. Specifically, the light transmitting plate includes a bottom surface 317, and the bottom surface 317 of the light transmitting plate may be further provided with a fluorescent layer, so as to further sharpen light emitted to the light transmitting plate, so that the width or area of light transmitted through the reflecting plate is smaller, and the position of the detector is identified or indicated more accurately. Certainly, it is also possible to provide no fluorescent layer, and sharpen reflected light using other physical or chemical methods.

Referring back to FIG. 3, the detector position indicating apparatus 300 further includes a reflecting unit 330 mounted at a lower side of the table panel assembly at a preset angle relative to the table panel assembly, and the reflecting unit 330 can reflect light emitted by the indicator light to cause the same to pass through the light transmitting plate.

Specifically, the reflecting unit 330 includes a first reflecting plate 331 provided between the first light emitting unit and the first light transmitting plate, a second reflecting plate 332 provided between the second light emitting unit and the second light transmitting plate, a third reflecting plate 333 provided between the third light emitting unit and the third light transmitting plate, and a fourth reflecting plate 334 provided between the fourth light emitting unit and the fourth light transmitting plate.

Specifically, the number and positions of the reflecting plates are related to the number and positions of the affixed light transmitting plates and light emitting units. For example, when only two light emitting units and only two light transmitting plates are provided, only two reflecting plates need to be provided. In addition, the length of the reflecting plate is substantially the same as or slightly greater than the length of the light transmitting plate.

In some embodiments, the reflecting plate is used to reflect light emitted by the light emitting unit so that the reflected light can be transmitted through the light transmitting plate, and thus, the shape and material of the reflecting plate are not limited. Two embodiments are shown in the present application, but those skilled in the art may also mount the reflecting plate in any other suitable manner.

Figure 8:
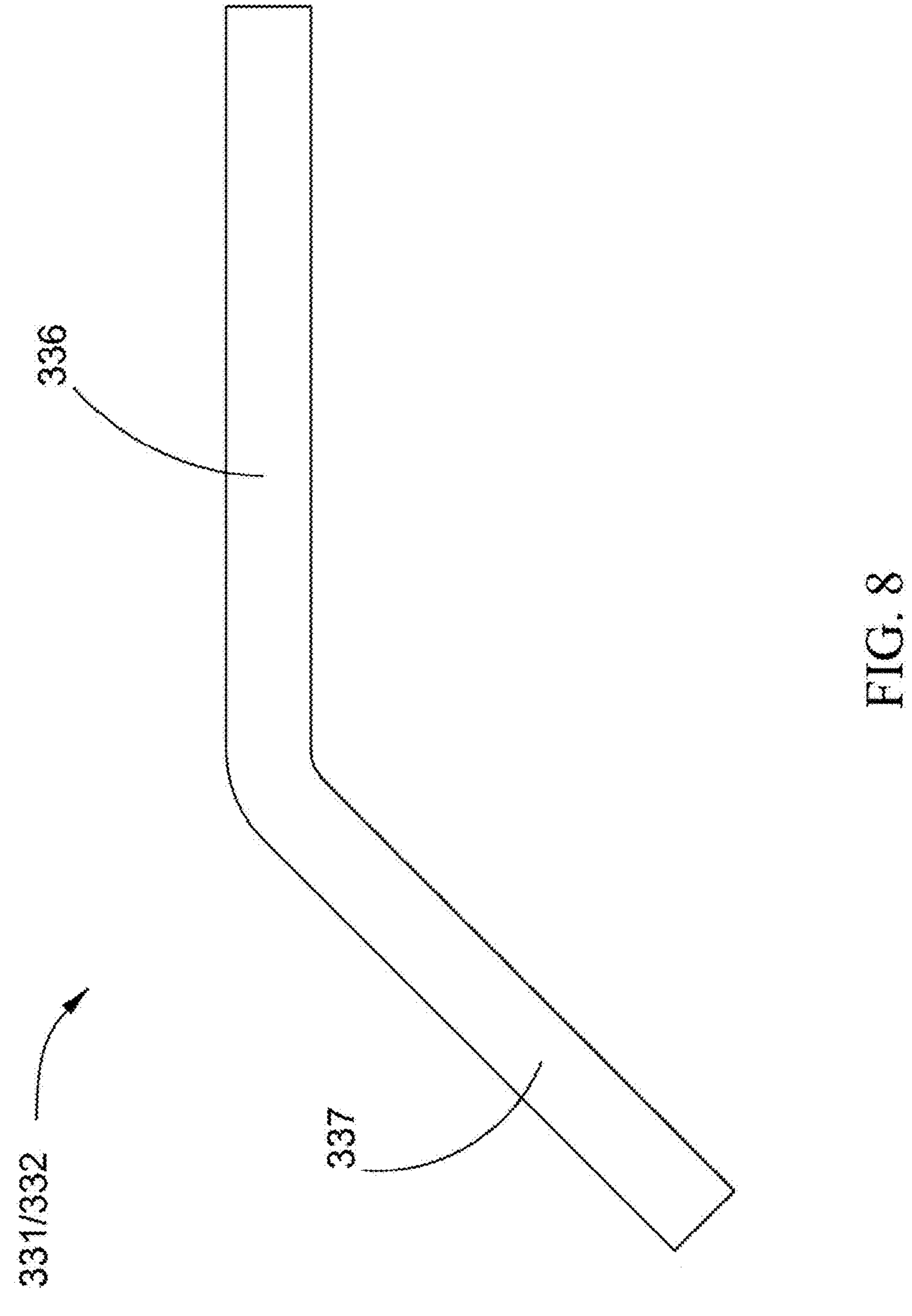
FIG. 8 is a cross-sectional view of a reflecting plate according to some embodiments of the present invention.

FIG. 8 shows a cross-sectional view of a reflecting plate according to some embodiments of the present invention. As shown in FIG. 8, the cross-sectional view of the reflecting plate shown in FIG. 8 corresponds to the cross-sectional view of the first reflecting plate 331 and the second reflecting plate 332 in FIG. 3. Specifically, the reflecting plate includes a mounting portion 336 and a reflecting portion 337. The mounting portion 336 is used to be fixed to a bottom surface of the table panel frame. For example, the mounting portion may be fixed to the table panel frame by means of a nut. Specifically, the mounting portion may be mounted at a position of an upper surface 205 (as shown in FIG. 3) of the bottom frame of the table panel frame, and the reflecting portion is configured to reflect the light emitted by the light emitting unit. The mounting portion and the reflecting portion are arranged to form a preset angle therebetween. For example, the angle between the mounting portion and the reflecting portion is greater than 90 degrees, and preferably, the included angle therebetween is approximately 135 degrees. Certainly, the angle may also be other values.

The length or size of the mounting portion and the length or size of the reflecting portion are determined according to the positional relationship and distance between the light emitting unit and the light transmitting plate. Specifically, the length of the mounting portion and the length of the reflecting portion are required not only to enable the light emitted by the light emitting unit to be reflected and direct the emitted light toward the light transmitting plate, but also to ensure that no other component between the light transmitting plate and the reflecting plate interferes with the light path. As described in the above embodiment, the light emitting unit may include a laser light, the laser light being capable of emitting a vertical laser line having a preset length, and such an arrangement can enable light to still be reflected to pass through the light transmitting plate when the reflecting plate is mounted with a deviation, or when there is a deviation in the included angle between the mounting portion and the reflecting portion.

In some embodiments, the reflecting portions 337 shown in FIG. 8 are all inwardly disposed. That is, the reflecting portions are all fixed in positions relatively close to the detector.

Figure 9:
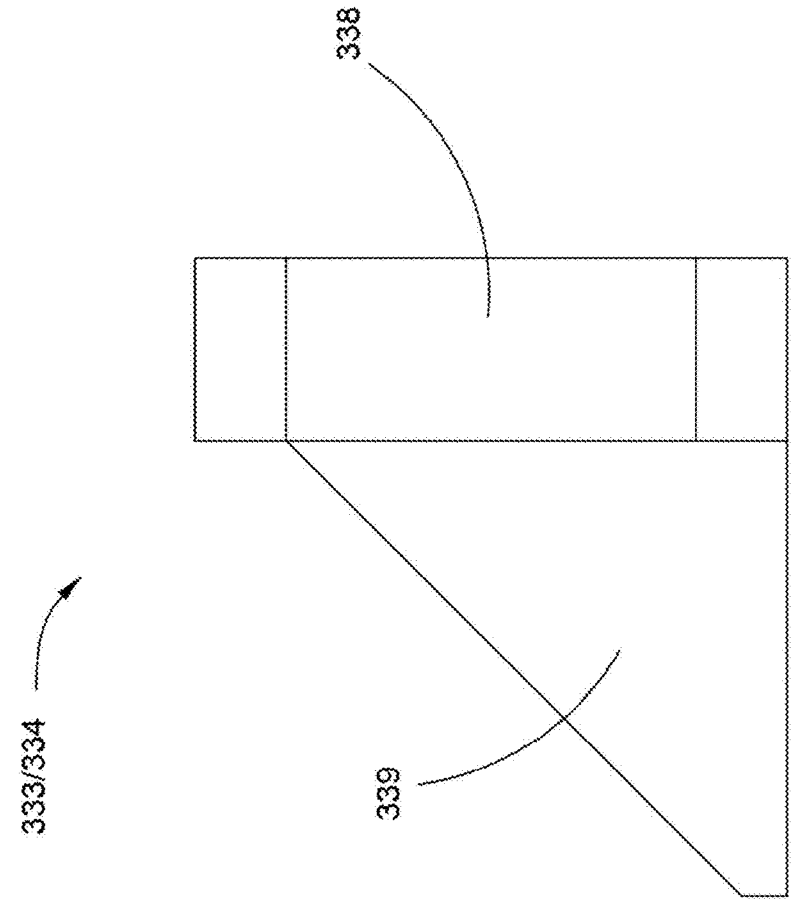
FIG. 9 is a cross-sectional view of a reflecting plate according to some other embodiments of the present invention.

FIG. 9 shows a cross-sectional view of a reflecting plate according to some other embodiments of the present invention. As shown in FIG. 9, the cross-sectional view of the reflecting plate shown in FIG. 9 corresponds to the cross-sectional view of the third reflecting plate 333 and the fourth reflecting plate 334 in FIG. 3. Specifically, the reflecting plate shown in FIG. 9 also includes a mounting portion 338 and a reflecting portion 339. Different from the reflecting plate shown in FIG. 8, the reflecting portion 339 in the reflecting plate shown in FIG. 9 has a substantially trapezoidal structure, and a preset included angle is present between a reflecting surface of the reflecting portion and the mounting portion or the table panel frame, and is preferably 45 degrees. Certainly, the reflecting portion may be triangular.

Similarly, the length or size of the mounting portion and the length or size of the reflecting portion are determined according to the positional relationship and distance between the light emitting unit and the light transmitting plate. Specifically, the length of the mounting portion and the length of the reflecting portion are required not only to enable the light emitted by the light emitting unit to be reflected and direct the emitted light toward the light transmitting plate, but also to ensure that no other component between the light transmitting plate and the reflecting plate interferes with the light path.

In some embodiments, the reflecting plate may be a mirror surface stainless steel plate, a polished mirror surface plate, or the like as long as the light can be reflected thereby.

Figure 10:
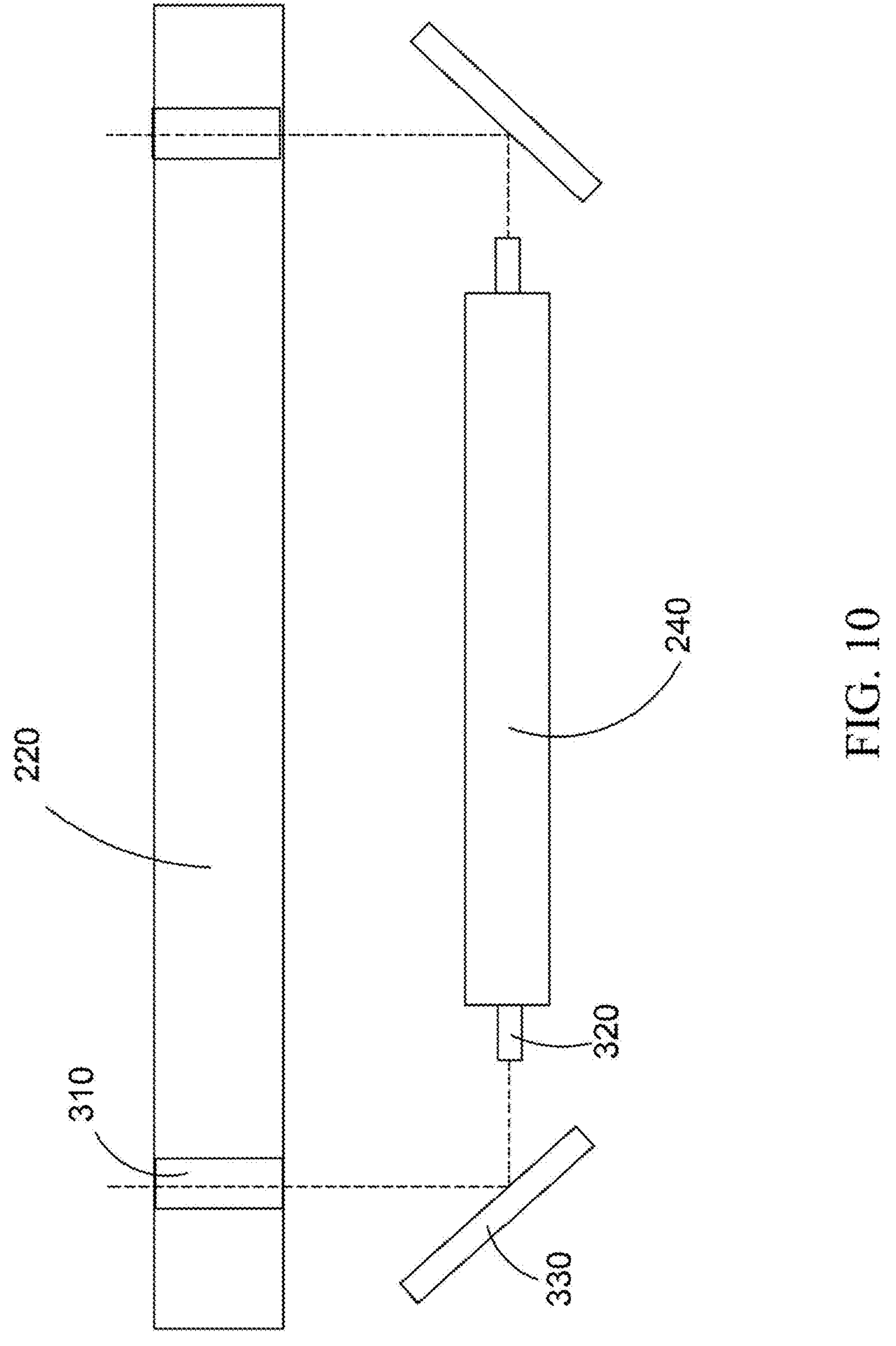
FIG. 10 is a schematic diagram of light reflection according to some embodiments of the present invention.

FIG. 10 shows a schematic diagram of light reflection according to some embodiments of the present invention. As shown in FIG. 10, the light emitting unit 320 mounted on the detector assembly 240 can emit light, and the light is reflected by the reflecting plate 330. The reflected light can be displayed via the light transmitting plate 310, thereby indicating the real-time position of the detector.

In some other embodiments, the detector position indicating apparatus may not be provided with any reflecting unit, but may further include a mounting unit (not shown) capable of fixing the indicator light to the detector cartridge, and light emitted by the indicator light can be directly aligned with the light transmitting plate without being reflected.

Figure 11:
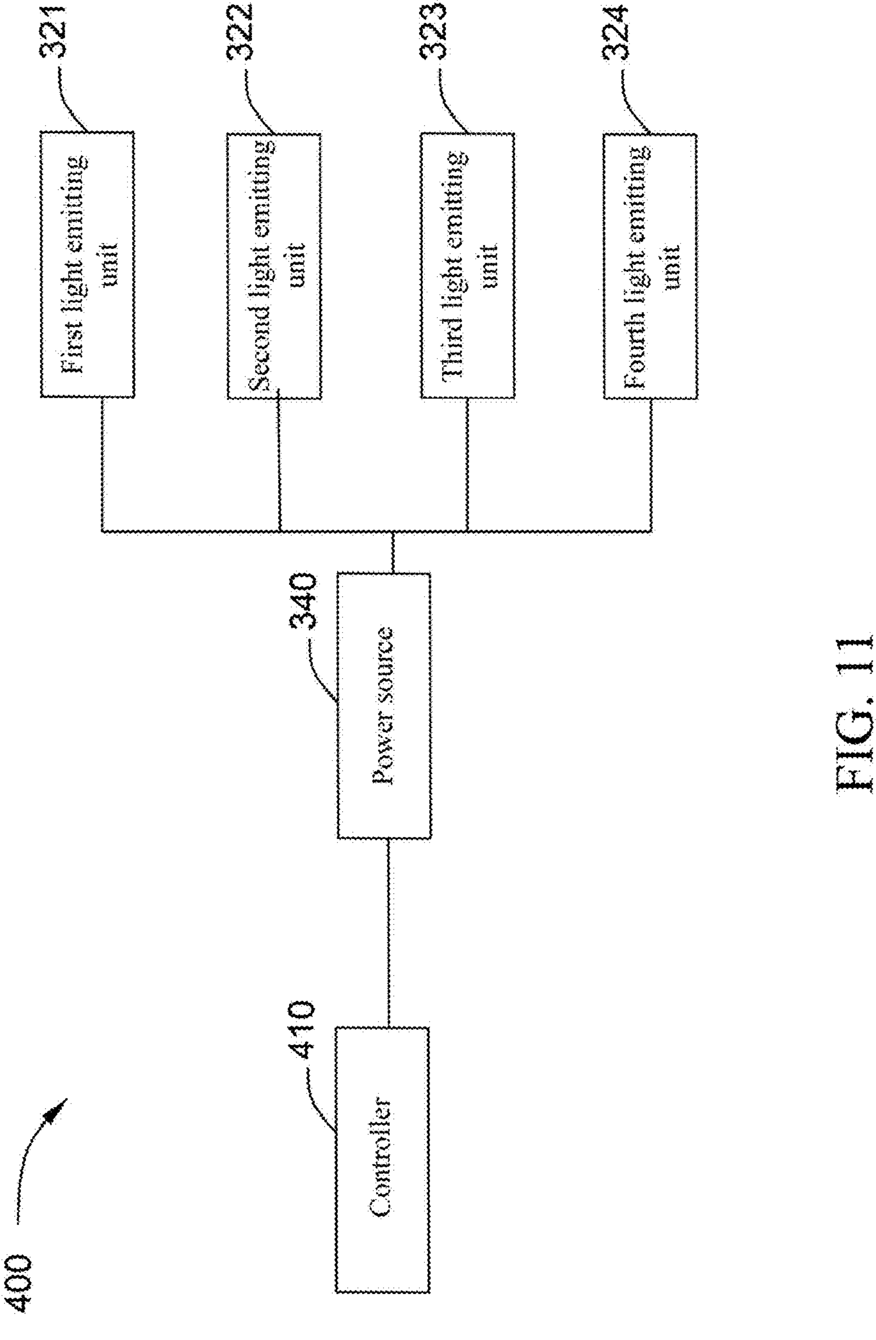
FIG. 11 is a schematic diagram of a control principle according to some embodiments of the present invention.

FIG. 11 is a schematic diagram of a control principle according to some embodiments of the present invention. As shown in FIG. 11, the detector position indicating apparatus further includes a power source 340, and the power source 340 can be connected to the light emitting unit in a wired or wireless manner to supply power to at least one light emitting unit. In an example having four light emitting units, the power source is separately connected to the first light emitting unit 321, the second light emitting unit 322, the third light emitting unit 323, and the fourth light emitting unit 324, and the power source 340 can supply power to the four light emitting units simultaneously. The power source 340 may be a rechargeable battery or another power source in the examination table.

The examination table further includes a controller 410 arranged within the base 210. The controller 410 can be connected to a control apparatus and/or an operator console of an X-ray imaging system, and can control the movement of the detector and/or the height adjustment of the examination table, so as to control the detector to move in the transverse direction and/or the longitudinal direction. The controller 410 controls the table panel and/or the detector on the basis of input signals from the pedal and/or input signals from the plurality of sensors.

In addition, the controller 410 can also be connected to the power source 340 in a wired or wireless manner to control the indicator light to turn on and off. Specifically, the controller can control light emitting unit to turn on and off via the power source 340. Certainly, in order to enable each light emitting unit to be controlled separately, a plurality of power sources may be provided to control each light emitting unit to turn on and off, respectively.

The controller can control the light emitting unit to turn on or off on the basis of an input signal or a feedback signal such as an input by a user, automatic detection of the movement of the detector cartridge, turning on of the table panel, and the like.

Specifically, the examination table further includes a sensor mounted on the table panel. The sensor is connected to the controller, and is mounted between the table panel and the table panel frame. When the sensor detects that the table panel is open, the controller controlling the indicator light to be turned off, so as to prevent light emitted by the indicator light from shining directly in the eyes of the user or the operator when the table panel is open.

Specifically, the controller can also be connected to a movement controller of the detector cartridge, and the movement controller can control the movement of the detector cartridge. When the movement controller controls the detector cartridge to start moving, a control signal is sent to the controller, and the controller automatically turns on the indicator light.

Certainly, a control switch may also be provided on the examination table or another control interface to turn the indicator light on or off on the basis of a user operation or input.

In the examination table according to some embodiments of the present invention, the light transmitting plate is provided on the table panel assembly, and the light emitting unit is provided on the detector assembly, so that light emitted by the light emitting unit can pass through the light transmitting plate to show the real-time position of the detector, thereby enabling the user to learn the real-time position of the detector easily. In addition, the light emitting units are provided on the two sides of the detector cartridge and the two ends of the bottom of the tray, respectively, so that not only it can be ensured that the moving path of the detector cartridge moving along the transverse axis is clear, but it can also be ensured that during movement along the transverse axis and/or the longitudinal axis, only one group of opposite light emitting units is displaced, and the other group of opposite light emitting units is not displaced, so as to accurately show the accurate position of the detector. Furthermore, the controller is connected to the light emitting unit, so that the light emitting unit can be controlled to turn on and off as desired, the position of the detector is not shown when real-time indication is not desired, and so on.

The present application provides the examination table according to some embodiments. The examination table includes a table panel and a detector cartridge. The detector cartridge is used to carry a detector, and is capable of moving the detector relative to the table panel, a coverage area of the detector constituting an imaging region. The examination table further includes a detector position indicating apparatus. The detector position indicating apparatus includes at least one light transmitting plate provided in a non-imaging region of the table panel and at least one light emitting unit fixed to the detector cartridge. The at least one light emitting unit includes an indicator light, and light emitted by the indicator light is capable of passing through the light transmitting plate to indicate a current position of the detector.

Specifically, the positions and the number of the light transmitting plates correspond to the positions and the number of the light emitting units.

Specifically, four borders of the table panel assembly are each provided with one light transmitting plate, and one light emitting unit is correspondingly mounted on four sides of the detector assembly.

Specifically, the light transmitting plate is configured to be in an elongated shape, and a length of the light transmitting plate is determined by a coverage area of the light emitting unit.

Specifically, the at least one light emitting unit is mounted at a center position of at least one side of the detector assembly.

Specifically, the indicator light includes a laser light, and light emitted by the laser light is a laser line having a preset length.

Specifically, the detector position indicating apparatus further includes a reflecting unit mounted at the bottom of the table panel assembly at a preset angle relative to the table panel assembly, and the reflecting unit is capable of reflecting light emitted by the indicator light so as to align the same with the light transmitting plate.

Specifically, the detector position indicating apparatus further includes a mounting unit capable of fixing the indicator light to the detector assembly, and light emitted by the indicator light is capable of being directly aligned with the light transmitting plate.

Specifically, the light transmitting plate has a protruding cross section, and the table panel assembly is provided with a recess corresponding to the protruding cross section, the light transmitting plate being capable of being mounted and fixed in the recess.

Specifically, a side of the light transmitting plate close to the indicator light is further provided with a fluorescent layer.

Specifically, the examination table further includes a controller capable of controlling the indicator light to turn on and off.

Specifically, the examination table further includes a sensor mounted on the table panel assembly, the sensor being connected to the controller, and when the sensor detects that the table panel assembly is open, the controller controlling the indicator light to be turned off.

The present application provides an X-ray imaging system according to some embodiments. The X-ray imaging system includes an examination table. The examination table includes a table panel and a detector cartridge. The detector cartridge is used to carry a detector, and is capable of moving the detector relative to the table panel, a coverage area of the detector constituting an imaging region. The examination table further includes a detector position indicating apparatus. The detector position indicating apparatus includes at least one light transmitting plate provided in a non-imaging region of the table panel and at least one light emitting unit fixed to the detector cartridge. The at least one light emitting unit includes an indicator light, and light emitted by the indicator light is capable of passing through the light transmitting plate to indicate a current position of the detector.

As used herein, the term "computer" may include any processor-based or microprocessor-based system, including a system using a microcontrol apparatus, a reduced instruction set computer (RISC), an application-specific integrated circuit (ASIC), a logic circuit, and any other circuit or processor capable of performing the functions described herein. The examples above are exemplary only and are not intended to limit the definition and/or meaning of the term "computer" in any way.

Some exemplary embodiments have been described above; however, it should be understood that various modifications may be made. For example, suitable results can be achieved if the described techniques are performed in a different order and/or if components in the described systems, architectures, devices, or circuits are combined in different ways and/or replaced or supplemented by additional components or equivalents thereof. Accordingly, other implementations also fall within the scope of protection of the claims.

The invention claimed is:

1. An examination table comprising:

a table panel assembly;

a detector assembly carrying a detector and being capable of moving the detector relative to the table panel assembly, wherein the detector assembly includes a coverage area constituting an imaging region; and a detector position indicating apparatus comprising:

at least one light transmitting plate provided in a non-imaging region of the table panel assembly, and at least one light emitting unit fixed to the detector assembly, the at least one light emitting unit comprising an indicator light, and light emitted by the indicator light being capable of passing through the at least one light transmitting plate to indicate a current position of the detector.

2. The examination table according to claim 1, wherein the positions and the number of the light transmitting plates correspond to the positions and the number of the light emitting units.

3. The examination table according to claim 1, wherein four borders of the table panel assembly are each provided with one light transmitting plate, and one light emitting unit is correspondingly mounted on four sides of the detector assembly.

4. The examination table according to claim 1, wherein the light transmitting plate is configured to be in an elongated shape, and a length of the light transmitting plate is determined by a coverage area of the light emitting unit.

5. The examination table according to claim 1, wherein the at least one light emitting unit is mounted at a center position of at least one side of the detector assembly.

6. The examination table according to claim 1, wherein the indicator light defines a laser light, and light emitted by the laser light is a laser line having a preset length.

7. The examination table according to claim 1, wherein the detector position indicating apparatus further includes a reflecting unit mounted at the bottom of the table panel assembly at a preset angle relative to the table panel assembly, and the reflecting unit is capable of reflecting light emitted by the indicator light so as to align same with the light transmitting plate.

8. The examination table according to claim 1, wherein the detector position indicating apparatus further comprises a mounting unit capable of fixing the indicator light to the detector assembly, and light emitted by the indicator light is capable of being directly aligned with the light transmitting plate.

9. The examination table according to claim 1, wherein the light transmitting plate has a protruding cross section, and the table panel assembly is provided with a recess corresponding to the protruding cross section, the light transmitting plate being capable of being mounted and fixed in the recess.

10. The examination table according to claim 1, wherein a side of the light transmitting plate close to the indicator light is further provided with a fluorescent layer.

11. The examination table according to claim 1, further comprising a controller capable of controlling the indicator light to turn on and off.

12. The examination table according to claim 11, further comprising a sensor mounted on the table panel assembly, the sensor being connected to the controller, and, when the sensor detects that the table panel assembly is open, the controller controlling the indicator light to be turned off.

* * * * *